(12) United States Patent
Kishore et al.

(10) Patent No.: US 12,196,621 B2
(45) Date of Patent: *Jan. 14, 2025

(54) SENSORS, METHODS, AND COMPUTER PROGRAM PRODUCTS FOR AIR BUBBLE DETECTION

(71) Applicant: Honeywell International Inc., Charlotte, NC (US)

(72) Inventors: Kuna Kishore, Hyderabad (IN); Scott Edward Beck, Murphy, TX (US)

(73) Assignee: Honeywell International Inc., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/516,759

(22) Filed: Nov. 21, 2023

(65) Prior Publication Data

US 2024/0085249 A1 Mar. 14, 2024

Related U.S. Application Data

(63) Continuation of application No. 17/078,902, filed on Oct. 23, 2020, now Pat. No. 11,860,042.

(51) Int. Cl.
*G01K 13/02* (2021.01)
*A61M 5/168* (2006.01)
(Continued)

(52) U.S. Cl.
CPC ......... *G01K 13/02* (2013.01); *A61M 5/16831* (2013.01); *G01K 1/024* (2013.01);
(Continued)

(58) Field of Classification Search
CPC .............................. G01K 7/021; G01K 15/002
See application file for complete search history.

(56) References Cited

U.S. PATENT DOCUMENTS 4,384,578 A * 5/1983 Winkler ............ A61M 5/16886
73/204.22
4,555,940 A * 12/1985 Renger ................. G01F 1/6847
604/246
(Continued)

FOREIGN PATENT DOCUMENTS

JP 2009-276323 A 11/2009
WO 2017/047224 A1 3/2017
WO 2020/132454 A1 6/2020

OTHER PUBLICATIONS

Decision to grant a European patent Mailed on Aug. 8, 2024 for EP Application No. 21203793, 2 page(s).
(Continued)

*Primary Examiner* — Nathaniel T Woodward
(74) *Attorney, Agent, or Firm* — Alston & Bird LLP

(57) ABSTRACT

Sensors, methods, and computer program products for air bubble detection are provided. An example method includes determining a first moving average for a first period of time based upon first temperature data and determining a second moving average for the first period of time based upon second temperature data. The method includes determining a first air presence parameter based upon a comparison between the first temperature data and the first moving average and a comparison between the second temperature data and the second moving average. The method includes determining a second air presence parameter based upon a comparison between the first temperature data, the second temperature data, and calibrated air thresholds. The method includes determining a third air presence parameter based upon a comparison between a first temperature data entry and each second temperature data entry. An air bubble within a fluid flow system is detected based upon the parameters.

20 Claims, 8 Drawing Sheets

(51) Int. Cl.
  *G01K 1/02* (2021.01)
  *G01K 1/024* (2021.01)
  *G01K 3/00* (2006.01)
  *G01K 7/02* (2021.01)
  *G05D 11/13* (2006.01)
  *G01K 13/024* (2021.01)

(52) U.S. Cl.
  CPC ............ *G01K 1/026* (2013.01); *G01K 3/005* (2013.01); *G01K 7/02* (2013.01); *G05D 11/135* (2013.01); *A61M 2205/3327* (2013.01); *A61M 2205/3368* (2013.01); *A61M 2205/50* (2013.01); *A61M 2205/702* (2013.01); *G01K 13/024* (2021.01); *G01K 13/026* (2021.01)

(56) References Cited

U.S. PATENT DOCUMENTS

| | | | | |
|---|---|---|---|---|
| 5,072,235 | A * | 12/1991 | Slowik | B41J 2/19 347/92 |
| 6,763,710 | B2 | 7/2004 | Mayer et al. | |
| 7,991,510 | B2 | 8/2011 | Duan et al. | |
| 10,254,142 | B2 | 4/2019 | Kostner et al. | |
| 10,842,950 | B2 * | 11/2020 | Peri | A61M 3/0204 |
| 11,860,042 | B2 | 1/2024 | Kishore et al. | |
| 2010/0143192 | A1 | 6/2010 | Myrick et al. | |
| 2011/0308328 | A1 * | 12/2011 | Haartsen | A61M 5/16886 73/861.41 |
| 2019/0054256 | A1 * | 2/2019 | Peri | A61M 5/365 |

OTHER PUBLICATIONS

Communication about intention to grant a European patent Mailed on Apr. 11, 2024 for EP Application No. 21203793, 6 page(s).
Extended European search report Mailed on Mar. 18, 2022 for EP Application No. 21203793, 9 page(s).
Non-Final Rejection Mailed on Jul. 28, 2023 for U.S. Appl. No. 17/078,902, 7 page(s).
Notice of Allowance and Fees Due (PTOL-85) Mailed on Aug. 21, 2023 for U.S. Appl. No. 17/078,902, 11 page(s).
U.S. Appl. No. 17/078,902, filed Oct. 23, 2020, U.S. Pat. No. 11,860,042, Patented.

* cited by examiner

SENSORS, METHODS, AND COMPUTER PROGRAM PRODUCTS FOR AIR BUBBLE DETECTION

CROSS-REFERENCE TO RELATED APPLICATIONS

This patent application is a continuation of U.S. patent application Ser. No. 17/078,902, filed Oct. 23, 2020, which is incorporated in its entirety herein by reference.

TECHNOLOGICAL FIELD

Example embodiments of the present disclosure relate generally to fluid flow systems and, more particularly, to the detection of air bubbles in fluid flow systems.

BACKGROUND

Fluid flow systems may be used in a multitude of applications in order to transport or otherwise move fluids from one location to another. For example, drug infusion pumps or other pharmaceutical delivery systems may transport drug solutions (e.g., liquid or fluid solutions) to a human patient. In such fluid flow systems, the presence of other materials (e.g., air bubbles, debris, etc.) may be detrimental to operation of the fluid flow system and/or harmful to, for example, a human patient. The inventors have identified numerous deficiencies with these existing technologies in the field, the remedies for which are the subject of the embodiments described herein.

BRIEF SUMMARY

As noted above, fluid flow systems may be used in a variety of contexts or applications in order to transport fluids or liquids. By way of example, industrial applications may transport chemicals, gels, fluids, solutions, etc. that may be prone to having air bubbles located within these fluids or may otherwise generated during operation as part of secondary reactions. These air bubbles may damage industrial equipment (e.g., via cavitation, pitting, etc.) as well as result in errors (e.g., inaccurate chemical compositions, incorrect delivery amounts, etc.) in operation of the equipment. In medical applications such as drug infusion pumps or pharmaceutical delivery systems, liquid medication may be provided to a human patient at a particular dosage such that the presence of any other material, debris, or air bubble within these medical applications may result in incorrect dosages and/or, in some instances, damage to the human patient (e.g., embolisms or the like). Conventional attempts at addressing these issues require separate air bubble detection modules (e.g., separate from the temperature sensors of the fluid flow system) that rely upon ultrasonic sensing technology or other non-invasive techniques that are often prone to false alarms (e.g., inaccurate results).

To solve these issues and others, example implementations of embodiments of the present disclosure may provide a temperature sensor configuration that may determine moving average temperature data for at least two (2) temperature sensors thermally coupled with a fluid flow system and use this temperature data to accurately detect the presence of an air bubble within the fluid flow system. Embodiments of the present disclosure may employ multiple air presence parameters relating to the moving averages, one or more calibrated air thresholds, and/or instantaneous temperature comparisons in order to further determine the volume of a detected air bubble and subsequently modify a fluid concentration rate of the fluid flow system. In doing so, such example implementations may reliably detect and confirm the presence of air bubbles in fluid flow systems as part of an integrated system component (e.g., without additional detection components).

Sensors, methods, system, devices, and associated computer program products are provided for air bubble detection. An example sensor for use with fluid flow systems may include a heating element, a first temperature sensor configured to generate first temperature data, and a second temperature sensor configured to generate second temperature data. The heating element, the first temperature sensor, and the second temperature sensor may be thermally coupled with a fluid flow system. The sensor may further include a controller operably coupled with the heating element, the first temperature sensor, and the second temperature sensor. The controller may be configured to determine a first moving average for a first period of time based upon the first temperature data generated by the first temperature sensor during the first period of time and determine a second moving average for the first period of time based upon the second temperature data generated by the second temperature sensor during the first period of time. The controller may further be configured to determine a first air presence parameter based upon a comparison between the first temperature data and the first moving average and a comparison between the second temperature data and the second moving average and determine a second air presence parameter based upon a comparison between the first temperature data, the second temperature data, and one or more calibrated air thresholds. The controller may also be configured to determine a third air presence parameter based upon a comparison between a first temperature data entry and each second temperature data entry and detect the presence of an air bubble within the fluid flow system based upon the first air presence parameter, the second air presence parameter, and the third air presence parameter.

In some embodiments, the second temperature sensor may be positioned downstream of the heating element, and the heating element is positioned downstream of the first temperature system relative to a fluid flow direction of the fluid flow system. In such an embodiment, the first temperature sensor may include a first pair of offset thermopiles, and the second temperature sensor may include a second pair of offset thermopiles.

In some embodiments, the controller may be further configured to compare each first temperature data entry generated by the first temperature sensor during the first period of time with the first moving average and compare each second temperature data entry generated by the second temperature sensor during the first period of time with the second moving average. In such an embodiment, the control may determine the first air presence parameter as a sum of the number of instances in which each first temperature data entry fails to exceed the first moving average and the number of instances in which each second temperature data entry fails to exceed the second moving average. The controller may subsequently compare the first air presence parameter with a first parameter threshold.

In some embodiments, the controller may be further configured to compare each first temperature data entry generated by the first temperature sensor during the first period of time with a first calibrated air threshold and compare each second temperature data entry generated by the second temperature sensor during the first period of time with a second calibrated air threshold. In such an embodiment, the controller may determine the second air presence parameter as a sum of the number of instances in which each first temperature data satisfies the first calibrated air threshold and the number of instances in which each second temperature data satisfies the second calibrated air threshold. The controller may subsequently compare the second air presence parameter with a second parameter threshold.

In some embodiments, the controller may compare at least a first temperature data entry generated by the first temperature sensor during the first period of time with each second temperature data entry generated by the second temperature sensor during the first period of time and determine the third air presence parameter as a sum of the number of instances in which the first temperature data entry is substantially equal to each second data entry. The controller may subsequently compare the third air presence parameter with a third parameter threshold.

In some further embodiments, the controller may be configured to determine a volume, length, and width of the air bubble within the fluid flow system based on the third air presence parameter.

In some still further embodiments, the controller may be further configured to modify a fluid concentration rate of the fluid flow system or generate an alert signal based upon the volume of the detected air bubble.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings. The components illustrated in the figures may or may not be present in certain embodiments described herein. Some embodiments may include fewer (or more) components than those shown in the figures.

DETAILED DESCRIPTION

Figure 1:
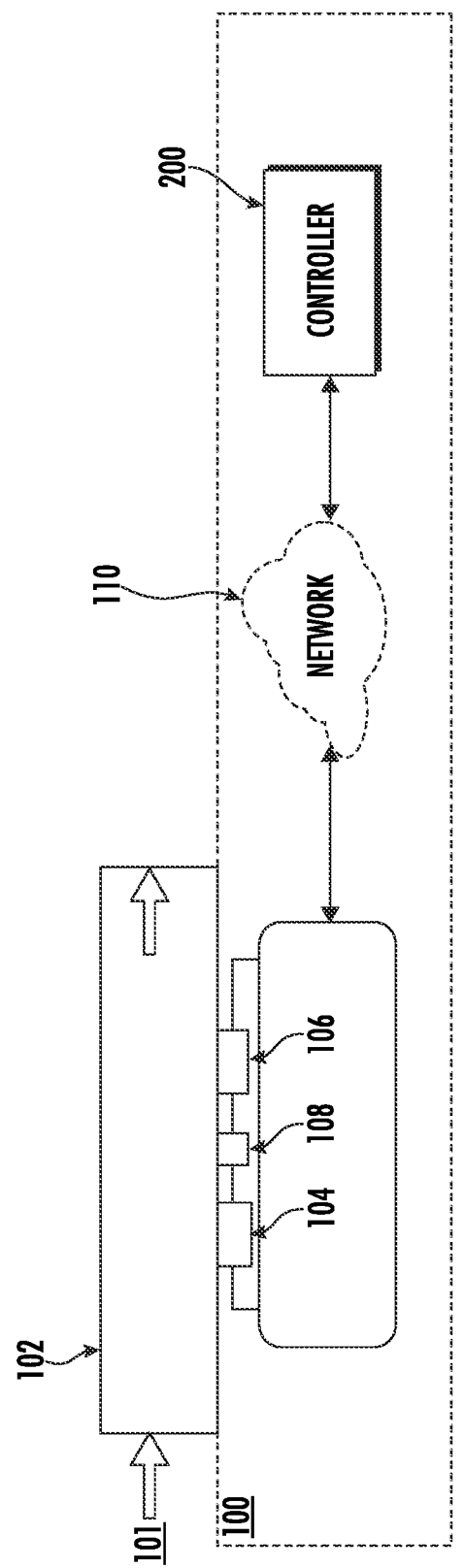
FIG. 1 illustrates an example sensor device and fluid flow system in accordance with some example embodiments described herein.
Figure 2A:
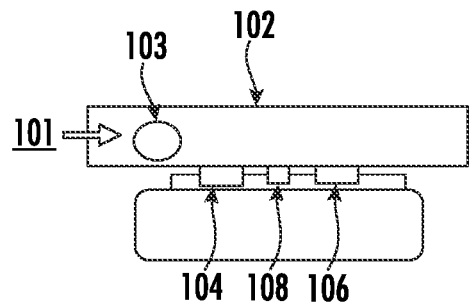
FIGS. 2A-2D illustrate an example air bubble within an example fluid flow system, in accordance with some example embodiments described herein.
Figure 2B:
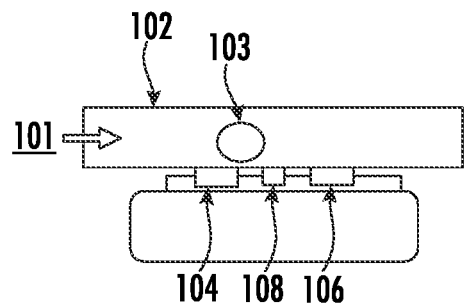
Figure 2C:
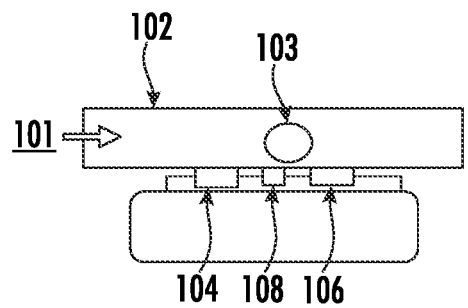
Figure 2D:
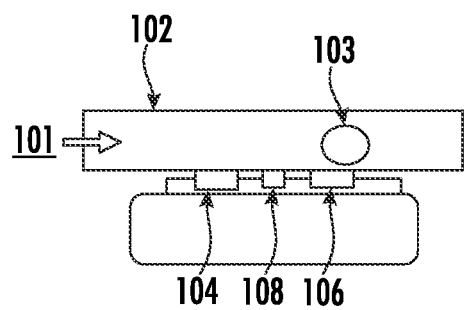

Some embodiments of the present disclosure will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used herein, the description may refer to a controller of an example sensor device as an example "apparatus." However, elements of the apparatus described herein may be equally applicable to the claimed method and computer program product. Thus, use of any such terms should not be taken to limit the spirit and scope of embodiments of the present invention.

Definition of Terms

As used herein, the terms "data," "content," "information," "electronic information," "signal," "command," and similar terms may be used interchangeably to refer to data capable of being transmitted, received, and/or stored in accordance with embodiments of the present disclosure. Thus, use of any such terms should not be taken to limit the spirit or scope of embodiments of the present disclosure. Further, where a first computing device is described herein to receive data from a second computing device, it will be appreciated that the data may be received directly from the second computing device or may be received indirectly via one or more intermediary computing devices, such as, for example, one or more servers, relays, routers, network access points, base stations, hosts, and/or the like, sometimes referred to herein as a "network." Similarly, where a first computing device is described herein as sending data to a second computing device, it will be appreciated that the data may be sent directly to the second computing device or may be sent indirectly via one or more intermediary computing devices, such as, for example, one or more servers, remote servers, cloud-based servers (e.g., cloud utilities), relays, routers, network access points, base stations, hosts, and/or the like.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

As used herein, the phrases "in one embodiment," "according to one embodiment," "in some embodiments," and the like generally refer to the fact that the particular feature, structure, or characteristic following the phrase may be included in at least one embodiment of the present disclosure. Thus, the particular feature, structure, or characteristic may be included in more than one embodiment of the present disclosure such that these phrases do not necessarily refer to the same embodiment.

As used herein, the word "example" is used herein to mean "serving as an example, instance, or illustration." Any implementation described herein as "example" is not necessarily to be construed as preferred or advantageous over other implementations.

As used herein, the terms "sensor" and "sensor device" refer to devices and associated computer hardware that is configured (either physically or by the execution of software) to generate temperature data associated with the temperature of a fluid flow. By way of example, the sensor device 100 of the present disclosure may include a first temperature sensor, a second temperature sensor, and a heating element that are configured to generate first temperature data, generate second temperature data, and generate heat, respectively. In some embodiments, the sensor or sensor device may include a "smart device" that is equipped with chip of other electronic device that is configured to communicate with a controller, computing device, or the like via Bluetooth, NFC, Wi-Fi, 3G, 4G, 5G protocols, and the like. In some embodiments, the sensor or sensor device may be configured to support or otherwise comprise the controller (e.g., the controller may be formed integral to or as part of the sensor device).

As used herein, the term "controller" refers to any user device, computing device, object, or system which may be in network communication with the first temperature sensor, the second temperature sensor, and/or the heating element. For example, the controller may refer to a wireless electronic device configured to perform various temperature related operations in response to temperature data generated by the first temperature sensor and/or the second temperature sensor. The controller may be configured to communicate with the first temperature sensor, the second temperature sensor, the heating element, and/or the like via Bluetooth, NFC, Wi-Fi, 3G, 4G, 5G protocols, and the like. In some instances, the controller may comprise the first temperature sensor, the second temperature sensor, and/or the heating element.

As used herein, the term "computer-readable medium" refers to non-transitory storage hardware, non-transitory storage device or non-transitory computer system memory that may be accessed by a controller, a microcontroller, a computational system or a module of a computational system to encode thereon computer-executable instructions or software programs. A non-transitory "computer-readable medium" may be accessed by a computational system or a module of a computational system to retrieve and/or execute the computer-executable instructions or software programs encoded on the medium. Exemplary non-transitory computer-readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM), and the like.

Having set forth a series of definitions called-upon throughout this application, an example system architecture and example apparatus is described below for implementing example embodiments and features of the present disclosure.

Device Architecture and Example Apparatus

With reference to FIG. 1, a fluid flow system 102 is illustrated with a sensor device 100. The fluid flow system 102 may define a fluid conduit (e.g., pipe, duct, or the like) through which fluid may flow. As described above, the fluid flow system 102 may be associated with an industrial application, medical application (e.g., infusion pump, pharmaceutical delivery system, etc.), or the like. As such, the fluid flow system 102 may be configured to support various gels, liquids, solutions, or other fluids as part of operation of such a fluid flow system 102. The fluid flow system 102 may define a fluid flow direction 101 that refers to a direction in which the fluid may flow within the fluid conduit. The fluid within the fluid flow system 102 may flow in a fluid flow direction 101 based upon an output of a pump, positive pressure, and/or the like. Although illustrated and described herein with reference to a fluid flow system 102 that includes a fluid flow direction 101, the present disclosure contemplates that the sensor device 100 described hereafter may be operable with any fluid flow system 102 regardless of configuration.

With reference to FIGS. 2A-2D, example movement of an air bubble 103 through the fluid flow system 102 is illustrated. During operation as shown, the air bubble 103 may propagate through the fluid flow system 102 in the fluid flow direction 101. The air bubble 103 may move through the fluid flow system 102 based upon the flow rate of the fluid flow system 102 (e.g., pressure supplied to the fluid flow system 102, cross-sectional area of the fluid conduit, etc.). As the air bubble 103 moves through the fluid flow system 102 (e.g., near the sensor device 100), the first temperature sensor 104 and/or the second temperature sensor 106 may detect a change in temperature proximate the respective sensors due to the thermal conductivity change within the fluid flow system 102 (e.g., the thermal conductivity of a fluid is greater than that of the air bubble 103) as described hereafter.

Turning back to FIG. 1, a sensor device 100 is illustrated that may be at least partially attached with the fluid flow system 102 in that the first temperature sensor 104, the second temperature sensor 106, and the heating element 108 may be in thermal engagement with the fluid within the fluid flow system 102. As shown, the sensor device 100 may further include a controller 200 operably coupled with the first temperature sensor 104, the second temperature sensor 106, and the heating element 108. Although the controller 200 is illustrated connected via a network 104, the present disclosure contemplates that, in some embodiments, the sensor device 100 may include the controller 200 such that the controller 200 may be in direct connection (e.g., physically connected) with the first temperature sensor 104, the second temperature sensor 106, and/or the heating element 108. By way of example, the sensor device 100 may define a housing or other enclosure configured to at least partially support one or more of the first temperature sensors 104, the second temperature sensors 106, the heating element 108, and/or the controller 200 therein. The sensor device 100 may define any housing, attachment mechanism, support structure, or the like, so long as thermal engagement is provided between the fluid flow system 102 and the temperature sensors 104, 106.

The heating element 108 may comprise any heat source configured to output thermal energy so as to heat or otherwise warm the fluid within the fluid flow system 102 proximate the heating element 108. By way of example, the heating element may comprise a resistive heating element in which the passage of electrical current through a resistor produces heat. Although described herein with reference to a resistive heating element 108, the present disclosure contemplates that any heating element (e.g., radiator, film heater, conductive heater, convective heater, etc.) may be used by the sensor device 100 so as to generate a thermal output (e.g., generate heat). As described hereafter, the controller 200 may also operate to maintain the thermal output of the heating element 108 so as to maintain a substantially (e.g., within applicable tolerances) constant thermal output of the heating element 108. Said differently, the sensor device 100 may employ a heating element 108 with a substantially constant thermal output so as to stabilize the temperature data generated by the first temperature sensor 104 and the second temperature sensor 106.

The sensor device 100 may include a first temperature sensor 104 that may be configured to generate first temperature data. As shown, the first temperature sensor 104 may be in thermal engagement with the fluid flow system 102 (e.g., in thermal engagement with the fluid within the fluid flow system 102) so as to determine the temperature within the fluid flow system 102 relative a first position of the first temperature sensor 104. In some embodiments, the first temperature sensor 104 may be positioned upstream (e.g., relative the fluid flow direction 101) of the heating element 108 and the second temperature sensor 106. By way of example, the first temperature sensor 104 may include a thermocouple, positive temperature coefficient (PTC) thermistor, negative temperature coefficient (NTC) thermistor, thermal anemometer, and/or the like configured to determine the temperature of the fluid proximate the first temperature sensor 104. Although illustrated with a single first temperature sensor 104, the present disclosure contemplates that the first temperature sensor 104 may further comprise a pair of offset thermopiles configured to, alone or in combination, generate first temperature data. Said differently, although described herein with reference to a single first temperature sensor 104 for convenience of description, the present disclosure contemplates that the techniques herein may be applicable to any number of first temperature sensors 104 positioned at any location with respect to the fluid flow system 102.

The sensor device 100 may include a second temperature sensor 106 that may be configured to generate second temperature data. As shown, the second temperature sensor 106 may be in thermal engagement with the fluid flow system 102 (e.g., in thermal engagement with the fluid within the fluid flow system 102) so as to determine the temperature within the fluid flow system 102 relative a second position of the second temperature sensor 106. In some embodiments, the second temperature sensor 106 may be positioned downstream (e.g., relative the fluid flow direction 101) of the heating element 108 and the first temperature sensor 104. By way of example, the second temperature sensor 106 may also include a thermocouple, positive temperature coefficient (PTC) thermistor, negative temperature coefficient (NTC) thermistor, thermal anemometer, and/or the like configured to determine the temperature of the fluid proximate the second temperature sensor 106. Although illustrated with a single second temperature sensor 106, the present disclosure contemplates that the second temperature sensor 106 may further comprise a pair of offset thermopiles configured to, alone or in combination, generate second temperature data. Said differently, although described herein with reference to a single second temperature sensor 106 for convenience of description, the present disclosure contemplates that the techniques herein may be applicable to any number of second temperature sensors 106 positioned at any location with respect to the fluid flow system 102.

In some example embodiments, the first temperature sensor 104 and/or the second temperature sensor 106 (or their equivalent functionality) may be positioned on the heating element 108. Said differently, the generation of temperature data as described herein may, in some embodiments, refer to temperature data generated near or on the heating element 108. By way of example, as an air bubble (e.g., air bubble 103 in FIGS. 2A-2D) passes by or is located proximate to the heating element 108, the resistance of the heating element 108 may also change due, at least in part, to the differences in heat capacity and thermal conductivity between gases and liquids as described above. As an air bubble (e.g., air bubble 103 in FIGS. 2A-2D) moves over a heating element 108 (e.g., a resistive heater) the temperature of the heating element 108 will increase, and the heating element's resistance will change based on the temperature coefficient of resistance of the material of the heating element 108.

Turning back to FIG. 1, the controller 200 may include circuitry, networked processors, or the like configured to perform some or all of the apparatus-based (e.g., sensor device-based) processes described herein, and may be any suitable processing device and/or network server. In this regard, the controller 200 may be embodied by any of a variety of devices. For example, the controller 200 may be configured to receive/transmit data (e.g., first temperature data and/or second temperature data) and may include any of a variety of fixed terminals, such as a server, desktop, or kiosk, or it may comprise any of a variety of mobile terminals, such as a portable digital assistant (PDA), mobile telephone, smartphone, laptop computer, tablet computer, or in some embodiments, a peripheral device that connects to one or more fixed or mobile terminals. Example embodiments contemplated herein may have various form factors and designs but will nevertheless include at least the components illustrated in FIG. 3 and described in connection therewith. In some embodiments, the controller 200 may be located remotely from the first temperature sensor 104 and/or the second temperature sensor 106, although in other embodiments, the controller 200 may comprise the first temperature sensor 104 and/or the second temperature sensor 106 in whole or in part. The controller 200 may, in some embodiments, comprise several servers or computing devices performing interconnected and/or distributed functions. Despite the many arrangements contemplated herein, the controller 200 is shown and described herein as a single computing device to avoid unnecessarily overcomplicating the disclosure. In some embodiments, one or more components of the controller 200 may be wholly or partially housed within one or more of the sensor device 100 and/or the fluid flow system 102.

The network 104 may include one or more wired and/or wireless communication networks including, for example, a wired or wireless local area network (LAN), personal area network (PAN), metropolitan area network (MAN), wide area network (WAN), or the like, as well as any hardware, software and/or firmware for implementing the one or more networks (e.g., network routers, switches, hubs, etc.). For example, the network 104 may include a cellular telephone, mobile broadband, long term evolution (LTE), GSM/EDGE, UMTS/HSPA, IEEE 802.11, IEEE 802.16, IEEE 802.20, Wi-Fi, dial-up, and/or WiMAX network. Furthermore, the network 104 may include a public network, such as the Internet, a private network, such as an intranet, or combinations thereof, and may utilize a variety of networking protocols now available or later developed including, but not limited to TCP/IP based networking protocols.

Figure 3:
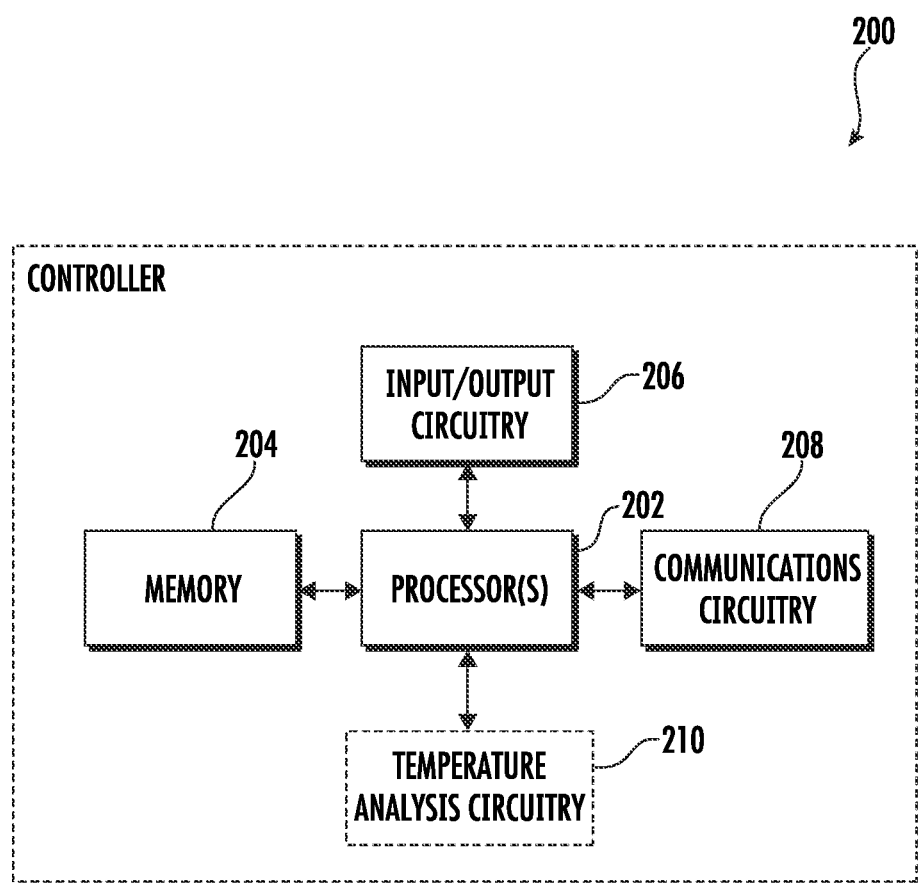
FIG. 3 illustrates a schematic block diagram of example circuitry that may perform various operations, in accordance with some example embodiments described herein.

As illustrated in FIG. 3, the controller 200 may include a processor 202, a memory 204, input/output circuitry 206, and communications circuitry 208. Moreover, the controller 200 may include temperature analysis circuitry 210. The controller 200 may be configured to execute the operations described below in connection with FIGS. 5-8. Although components 202-210 are described in some cases using functional language, it should be understood that the particular implementations necessarily include the use of particular hardware. It should also be understood that certain of these components 202-210 may include similar or common hardware. For example, two sets of circuitry may both leverage use of the same processor 202, memory 204, communications circuitry 208, or the like to perform their associated functions, such that duplicate hardware is not required for each set of circuitry. The use of the term "circuitry" as used herein includes particular hardware configured to perform the functions associated with respective circuitry described herein. As described in the example above, in some embodiments, various elements or components of the circuitry of the controller 200 may be housed within the sensor device 100. It will be understood in this regard that some of the components described in connection with the controller 200 may be housed within one or more of the device of FIG. 1, while other components are housed within another of these devices, or by yet another device not expressly illustrated in FIG. 1.

Of course, while the term "circuitry" should be understood broadly to include hardware, in some embodiments, the term "circuitry" may also include software for configuring the hardware. For example, although "circuitry" may include processing circuitry, storage media, network interfaces, input/output devices, and the like, other elements of the controller 200 may provide or supplement the functionality of particular circuitry.

In some embodiments, the processor 202 (and/or coprocessor or any other processing circuitry assisting or otherwise associated with the processor) may be in communication with the memory 204 via a bus for passing information among components of the controller 200. The memory 204 may be non-transitory and may include, for example, one or more volatile and/or non-volatile memories. In other words, for example, the memory may be an electronic storage device (e.g., a non-transitory computer readable storage medium). The memory 204 may be configured to store information, data, content, applications, instructions, or the like, for enabling the controller 200 to carry out various functions in accordance with example embodiments of the present invention.

The processor 202 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the computing device, and/or remote or "cloud" processors.

In an example embodiment, the processor 202 may be configured to execute instructions stored in the memory 204 or otherwise accessible to the processor 202. Alternatively or additionally, the processor 202 may be configured to execute hard-coded functionality. As such, whether configured by hardware or by a combination of hardware with software, the processor 202 may represent an entity (e.g., physically embodied in circuitry) capable of performing operations according to an embodiment of the present invention while configured accordingly. Alternatively, as another example, when the processor 202 is embodied as an executor of software instructions, the instructions may specifically configure the processor 202 to perform the algorithms and/or operations described herein when the instructions are executed.

The controller 200 further includes input/output circuitry 206 that may, in turn, be in communication with processor 202 to provide output to a user and to receive input from a user, user device, or another source. In this regard, the input/output circuitry 206 may comprise a display that may be manipulated by a mobile application. In some embodiments, the input/output circuitry 206 may also include additional functionality including a keyboard, a mouse, a joystick, a touch screen, touch areas, soft keys, a microphone, a speaker, or other input/output mechanisms. The processor 202 and/or user interface circuitry comprising the processor 202 may be configured to control one or more functions of a display through computer program instructions (e.g., software and/or firmware) stored on a memory accessible to the processor (e.g., memory 204, and/or the like).

The communications circuitry 208 may be any means such as a device or circuitry embodied in either hardware or a combination of hardware and software that is configured to receive and/or transmit data from/to a network and/or any other device, circuitry, or module in communication with the controller 200. In this regard, the communications circuitry 208 may include, for example, a network interface for enabling communications with a wired or wireless communication network. For example, the communications circuitry 208 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s). These signals may be transmitted by the controller 200 using any of a number of wireless personal area network (PAN) technologies, such as Bluetooth® v1.0 through v3.0, Bluetooth Low Energy (BLE), infrared wireless (e.g., IrDA), ultra-wideband (UWB), induction wireless transmission, or the like. In addition, it should be understood that these signals may be transmitted using Wi-Fi, Near Field Communications (NFC), Worldwide Interoperability for Microwave Access (WiMAX) or other proximity-based communications protocols.

Temperature analysis circuitry 210 includes hardware components designed to generate a first moving average and a second moving average based upon respective temperature data. Temperature analysis circuitry 210 may utilize processing circuitry, such as the processor 202, to perform its corresponding operations, and may utilize memory 204 to store collected information. In some instances, the temperature analysis circuitry 210 may be configured to determine a first air presence parameter based upon a comparison between the first temperature data and the first moving average and a comparison between the second temperature data and the second moving average. The temperature analysis circuitry 210 may be also configured to determine a second air presence parameter based upon a comparison between the first temperature data, the second temperature data, and one or more calibrated air thresholds and determine a third air presence parameter based upon a comparison between a first temperature data entry and each second temperature data entry.

It should also be appreciated that, in some embodiments, the temperature analysis circuitry 210 may include a separate processor, specially configured field programmable gate array (FPGA), or application specific interface circuit (ASIC) to perform its corresponding functions.

In addition, computer program instructions and/or other type of code may be loaded onto a computer, processor or other programmable circuitry to produce a machine, such that the computer, processor other programmable circuitry that execute the code on the machine create the means for implementing the various functions, including those described in connection with the components of controller 200.

As described above and as will be appreciated based on this disclosure, embodiments of the present invention may be configured as sensors, methods, and the like. Accordingly, embodiments may comprise various means including entirely of hardware or any combination of software with hardware. Furthermore, embodiments may take the form of a computer program product comprising instructions stored on at least one non-transitory computer-readable storage medium (e.g., computer software stored on a hardware device). Any suitable computer-readable storage medium may be utilized including non-transitory hard disks, CD-ROMs, flash memory, optical storage devices, or magnetic storage devices.

Figure 4:
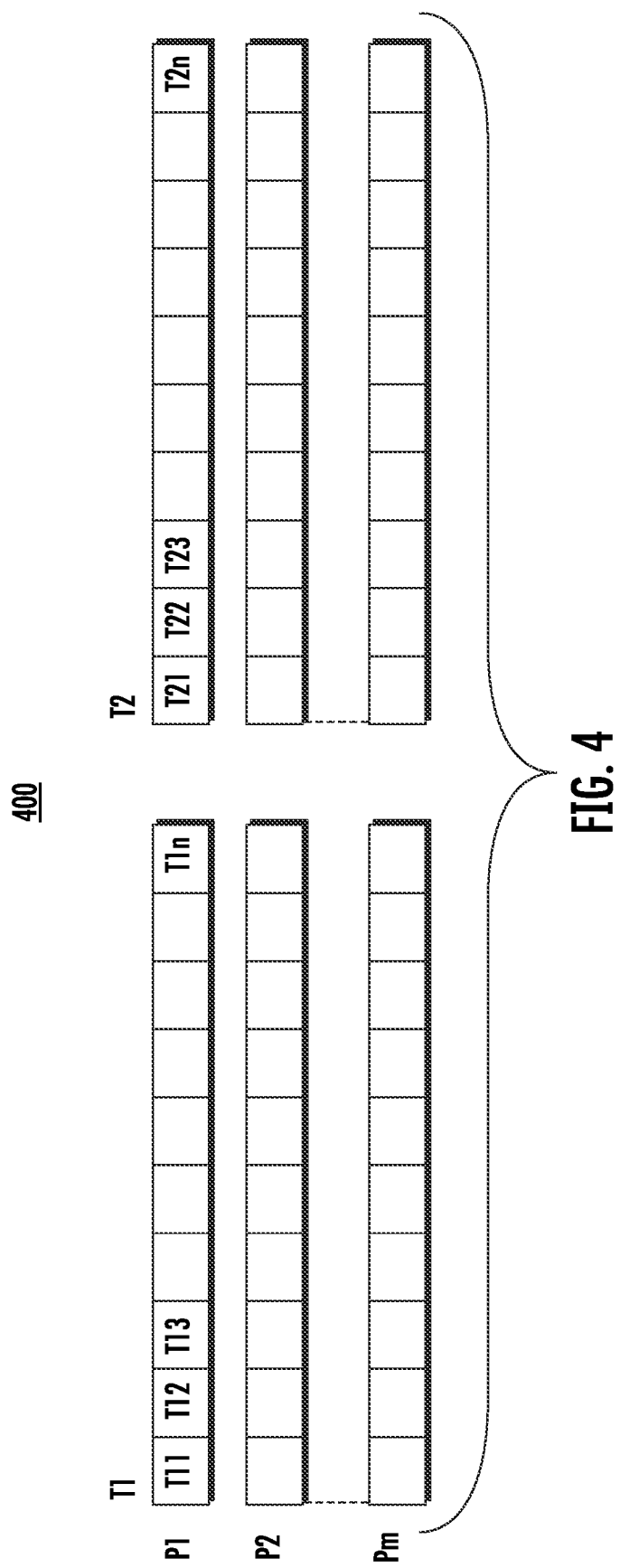
FIG. 4 illustrates example first temperature data and example second temperature data, in accordance with some example embodiments described herein.

With reference to FIG. 4, example first temperature data and example second temperature data are illustrated. As described above and further hereafter, the first temperature sensor 104 may generate first temperature data that that may, for example, refer to a detected voltage change by the first temperature sensor 104. In some embodiments, the first temperature sensor 104 may be configured to determine an associated temperature value associated with the detected voltage change. In other embodiments, the first temperature sensor 104 may transmit the detected voltage change to the controller 200, and the controller 200 may determine the temperature value associated with the voltage change. Similarly, the second temperature sensor 106 may, in some embodiments, be configured to determine an associated temperature value associated with the detected voltage change. In other embodiments, the second temperature sensor 106 may transmit the detected voltage change to the controller 200, and the controller 200 may determine the temperature value associated with the voltage change.

In any embodiment, the first temperature data and the second temperature data generated by the first temperature sensor 104 and the second temperature sensor 106, respectively, may be generated with an associated time data entry (e.g., timestamped) indicative of the time at which the respective temperature data is generated. As shown in FIG. 4, the first temperature data and the second temperature data may be collected in datasets (e.g. P1, P2, . . . , Pm). Each dataset may include a defined number (n) of data samples (e.g., timestamped temperature data entries). By way of a particular example, the first temperature sensor 104 may generate first temperature data that includes, for example, fifty (50) timestamped first temperature data entries (e.g., T11, T12, . . . , T150). Similarly, the second temperature sensor 106 may generate second temperature data that includes, for example, fifty (50) timestamped second temperature data entries (e.g., T21, T22, . . . , T250). In embodiments in which the first temperature sensor 104 and/or the second temperature sensor 106 include offset thermopiles or other additional sensors, the datasets described herein may also include such temperature data entries. Additionally, the first temperature sensor 104 and the second temperature sensor 106 may be configured to generate first temperature data and second temperature data, respectively, based upon an associated testing or sample rate of these sensors 104, 106 (e.g., a sampling rate of 1 millisecond or the like). Although described herein with reference to an example fifty (5) number of data samples n, the present disclosure contemplates that any number of data samples may be used. Said differently, the number of data entries n is determined by a sampling rate of the respective temperature sensor multiplied by any suitable multiplier integer to cover a reasonable length of time to calculate moving average.

With continued reference to FIG. 4, the first temperature sensor 104 and the second temperature sensor 106 may further includes a plurality of groups of timestamped temperature data entries or multiple datasets. These datasets may, in some embodiments, refer to temperature data entries generated during a particular time period associated with the dataset. In some further embodiments, temperature data entries within each dataset may be compared against a moving average of the respective dataset and/or against other temperature data entries of the respective dataset as described hereafter. For the sake of convenience of description, example operations hereafter are described with reference to a single dataset (e.g. P1) of first temperature data and second temperature data (e.g., an embodiment in which the air bubble 103 passes by the sensor device 100 during a single dataset P1 of time).

Example Operations for Air Bubble Detection

Figure 5:
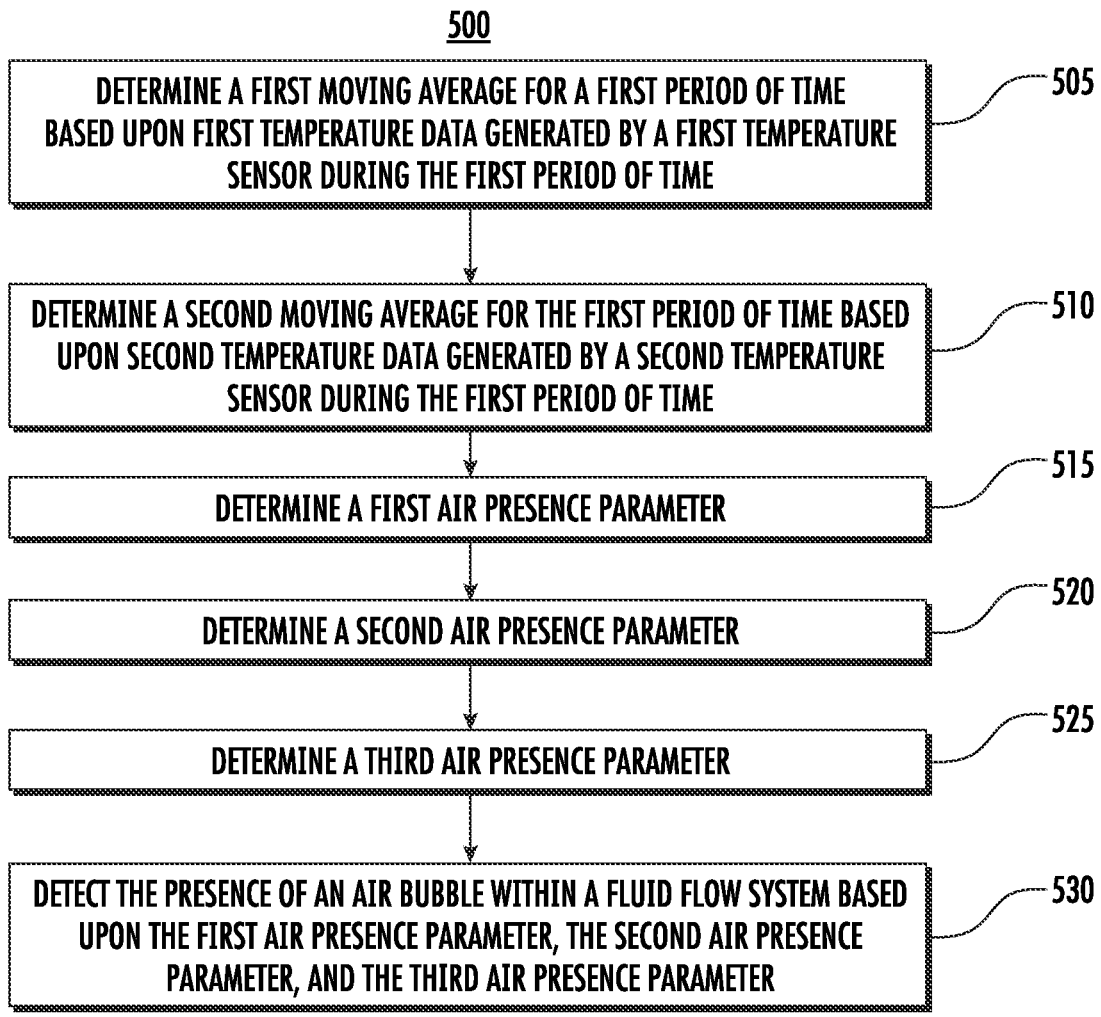
FIG. 5 illustrates an example flowchart for air bubble detection, in accordance with some example embodiments described herein.

FIG. 5 illustrates a flowchart containing a series of operations for air bubble detection. The operations illustrated in FIG. 5 may, for example, be performed by, with the assistance of, and/or under the control of an apparatus (e.g., sensor device 100 and/or controller 200), as described above. In this regard, performance of the operations may invoke one or more of processor 202, memory 204, input/output circuitry 206, communications circuitry 208, and/or temperature analysis circuitry 210.

As shown in operation 505, the apparatus (e.g., sensor derive 100 and/or controller 200) includes means, such as processor 202, communications circuitry 208, temperature analysis circuitry 210, or the like, for determining a first moving average for a first period of time based upon first temperature data generated by a first temperature sensor during the first period of time. As described above, the first temperature sensor 104 may be configured to periodically generate first temperature data (e.g., based upon a sampling rate) over a first period of time associated with the dataset (e.g., dataset P1). The first period of time may include any number of first temperature data entries with associated timestamps based upon the sampling rate of the first temperature sensor 104. The first period of time may, in some embodiments, be determined based upon a fluid flow rate of the fluid flow system 102. Said differently, the first period of time may be defined to accommodate for the flow velocity at which a potential air bubble may travel through the fluid flow system 102. For example, a longer in time first time period may be used for relatively slower flow rates, while a shorter in time first time period may be use for relatively faster flow rates. The number of datasets m to be considered by the systems described herein for bubble determination may depend upon the prevailing fluid flow rate within the fluid flow system 102 and the temperature sampling rate described above. For example, a slower flow rate may require an increased number of datasets m to increase the system's bubble detection confidence.

As described herein, an average or mean refers to the sum of the value of the data entries (e.g., the sum of the first temperature values associated with the first temperature data entries) divided by the number of data entries (e.g., the number of first temperature data entries within the first dataset). A moving average (e.g., rolling average, running average, or the like) refers to a calculation in which a series of averages of different subsets are used. For example an average of a portion of the first dataset may be calculated. By way of an additional example, in some instances, a plurality of datasets (e.g., P1, P2, . . . , Pm) represent subsets of the full dataset (e.g., the total collection of temperature data entries). As such, an average of the first dataset P1 may represent a moving average for subsequent in time first temperature data entries. By way of a further example, the first dataset P1 may be iteratively updated while maintaining a determined size in that the oldest in time entry is removed from the first dataset as a most recent in time entry is added to the dataset. In this way, the first moving average comprises the iteratively determined average of the first temperature data entries. Regardless of the number of first temperature data entries generated during the first period of time, the controller 200 may be configured to determine a first moving average of these first temperature data entries for this first period of time.

As shown in operation 510, the apparatus (e.g., sensor derive 100 and/or controller 200) includes means, such as processor 202, communications circuitry 208, temperature analysis circuitry 210, or the like, for determining a second moving average for the first period of time based upon second temperature data generated by a second temperature sensor during the first period of time. Similar to operation 505, the second temperature sensor 106 may be configured to periodically generate second temperature data (e.g., based upon a sampling rate) over the first period of time associated with the dataset (e.g., dataset P1). As described herein, an average or mean refers to the sum of the value of the data entries (e.g., the sum of the second temperature values associated with the second temperature data entries) divided by the number of data entries (e.g., the number of second temperature data entries within the first dataset). A moving average (e.g., rolling average, running average, or the like) refers to a calculation in which a series of averages of different subsets are used. For example an average of a subset of the first dataset may be calculated. By way of an additional example, in some instances, a plurality of datasets (e.g., P1, P2, . . . , Pm) represent subsets of the full dataset (e.g., the total collection of temperature data entries). As such, an average of the first dataset P1 may represent a moving average for subsequent in time second temperature data entries. By way of a further example, the first dataset P1 may be iteratively updated while maintaining a determined size in that the oldest in time entry is removed from the first dataset as a most recent in time entry is added to the dataset. In this way, the second moving average comprises the iteratively determined average of the second temperature data entries of the first dataset. Regardless of the number of second temperature data entries generated during the first period of time, the controller 200 may be configured to determine a second moving average of these second temperature data entries for this first period of time.

As shown in operation 515, the apparatus (e.g., sensor derive 100 and/or controller 200) includes means, such as processor 202, communications circuitry 208, temperature analysis circuitry 210, or the like, for determining a first air presence parameter. The determination at operation 515 may be based upon a comparison between the first temperature data and the first moving average, and a comparison between the second temperature data and the second moving average. As described hereafter with reference to FIG. 6, the first presence parameter may be used to analyze for momentary drift of measured temperature (e.g., first temperature data and/or second temperature data) as a result of the presence of an air bubble 103 within the fluid flow system 102. Said differently, the comparison between instantaneous temperature data entries (e.g., between first temperature data and the first moving average and between second temperature data and the second moving average) may operate to accurately detect a momentary change (e.g., an instantaneous temperature value that is less than that of the moving average) indicative of the presence of an air bubble 103.

As shown in operation 520, the apparatus (e.g., sensor derive 100 and/or controller 200) includes means, such as processor 202, communications circuitry 208, temperature analysis circuitry 210, or the like, for determining a second air presence parameter. The determination at operation 520 may be based upon a comparison between the first temperature data, the second temperature data, and one or more calibrated air thresholds. As described hereafter with reference to FIG. 7, the sensor device 100 and/or controller 200 may be configured to receive calibrated air thresholds and/or determine calibrated air thresholds associated with each of the first temperature sensor 104 and the second temperature sensor 106. As described hereafter, the fluid flow system 102 may be supplied with air (e.g., an absence of fluid flow) and the first temperature data entries may be used to determine a first calibrated air threshold. The second temperature data entries may be similarly used to determine a second calibrated air threshold. These calibrated air thresholds may be indicative of a known or otherwise valid temperature value (s) associated with air flow and/or air bubbles. Such a comparison between the first temperature data entries and the second temperature data entries and the one or more calibrated air thresholds may operate to establish a confidence in the air bubble presence that is independent of fluid flow rate. Said differently, flow rate related temperature changes may be removed from consideration by the controller 200 in performing the determination of the second air presence parameter.

As shown in operation 525, the apparatus (e.g., sensor derive 100 and/or controller 200) includes means, such as processor 202, communications circuitry 208, temperature analysis circuitry 210, or the like, for determining a third air presence parameter. The determination at operation 525 may be based upon a comparison between a first temperature data entry and each second temperature data entry. As described hereafter with reference to FIG. 8, the sensor device 100 and/or controller 200 may be configured to identify a shift in momentary temperate change indicative of the leading and/ or trailing edges of the air bubble 103 (e.g., the front or end of the air bubble 103). Said differently, a comparison between upstream temperature data (e.g., first temperature data) and downstream temperature data (e.g., second temperature data) may be used to identify substantially equal (e.g., within applicable tolerances) temperature data entries in order to identify a leading and/or trailing edge of the air bubble. As further described hereafter, the size (e.g., length and width) and/or volume of the air bubble 103 may, in some embodiments, be determined based upon the third air presence parameter (e.g., based upon the detected edges of the air bubble 103).

Thereafter, as shown in operation 530, the apparatus (e.g., sensor derive 100 and/or controller 200) includes means, such as processor 202, communications circuitry 208, temperature analysis circuitry 210, or the like, for detecting the presence of an air bubble 103 within a fluid flow system 102 based upon the first air presence parameter, the second air presence parameter, and the third air presence parameter. As described hereafter with reference to FIGS. 6-8, the first air presence parameter, the second air presence parameter, and the third air presence parameter may be compared against respective thresholds in order to increase the controller 200's confidence or otherwise validate the presence of an air bubble 103 within the fluid flow system 102. By way of example, the thresholds described hereafter may refer to a minimum portion (e.g., >50%) of the total number of temperature data entries (e.g., n samples×m datasets) against which the respective air presence parameters may be compared. In an instance in which the first air presence parameter satisfies the first parameter threshold, in which the second air presence parameter satisfies the second parameter threshold, and in which the third air presence parameter satisfies the third parameter threshold, the controller 200 may detect the presence of the air bubble 103.

Figure 6:
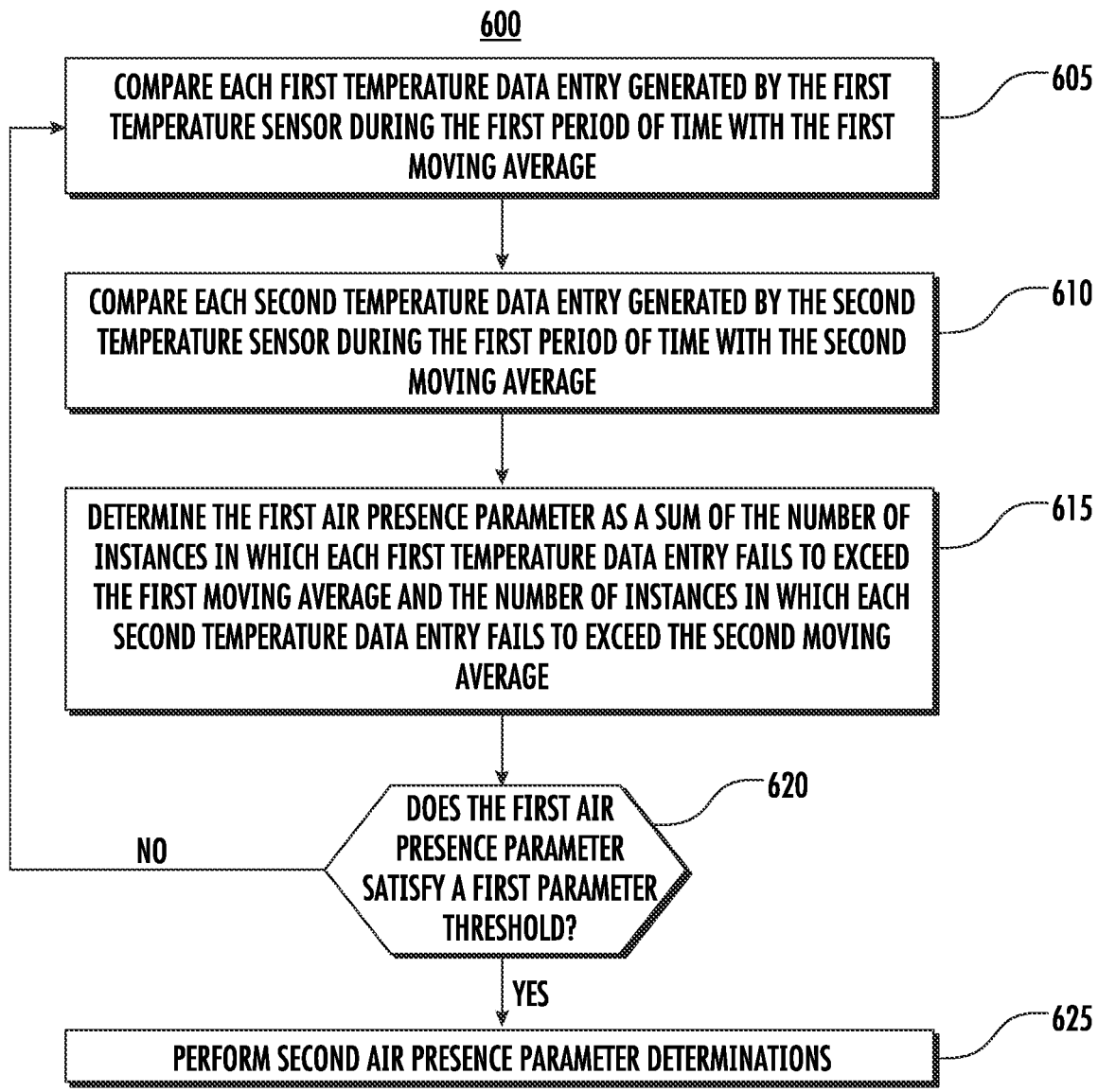
FIG. 6 illustrates an example flowchart for first air presence parameter determinations, in accordance with some example embodiments described herein.

FIG. 6 illustrates a flowchart containing a series of operations for first air presence parameter determinations. The operations illustrated in FIG. 6 may, for example, be performed by, with the assistance of, and/or under the control of an apparatus (e.g., sensor device 100 and/or controller 200), as described above. In this regard, performance of the operations may invoke one or more of processor 202, memory 204, input/output circuitry 206, communications circuitry 208, and/or temperature analysis circuitry 210.

As shown in operation 605, the apparatus (e.g., sensor derive 100 and/or controller 200) includes means, such as processor 202, communications circuitry 208, temperature analysis circuitry 210, or the like, for comparing each first temperature data entry generated by the first temperature sensor 104 during the first period of time with the first moving average. As described above, the first temperature sensor 104 may generate first temperature data entries (e.g., T11, T12, ..., TiN) as part of a first dataset P1 over a first period of time (e.g., resulting in n number of first temperature data entries). By way of example, controller 200 may analyze a first dataset P1 that includes, for example, fifty (50) first temperature data entries (e.g., an n of 50). The controller 200 may generate a first moving average as described above with reference to operation 505 that includes a sum of each first temperature data entry of the first dataset P1 divided by the total number of first temperature data entries n. By way of a particular example, the first moving average may be determined to be 30° C. such that each first temperature data entry (e.g., T12, T12, ..., T150) of the first dataset P1 may be compared against the first moving average.

As described hereafter with reference to operation 615, the controller 200 may operate to count (and subsequently sum) the number of instances in which each first temperature data entry fails to exceed (e.g., is less than) the first moving average (e.g., is <30° C.). As described above, the thermal conductivity of a fluid is greater than that of the air bubble 103. As such, a comparison between each first temperature data entry and the first moving average may identify first temperature data entries that are less than the first moving average of the first temperature sensor 104 that may be indicative of the presence of an air bubble 103 proximate the first temperature sensor 104. Although described herein with reference to a single dataset P1 that includes fifty (50) first temperature data entries and a first moving average of 30° C., the present disclosure contemplates that the operations described herein may be applicable to any number of datasets comprising any number of first temperature data entries and the first moving average may be determined to be any temperature value.

As shown in operation 610, the apparatus (e.g., sensor derive 100 and/or controller 200) includes means, such as processor 202, communications circuitry 208, temperature analysis circuitry 210, or the like, for comparing each second temperature data entry generated by the second temperature sensor 106 during the first period of time with the second moving average. As described above, the second temperature sensor 106 may generate second temperature data entries (e.g., T21, T22, ..., T2N) as part of a first dataset P1 over the first period of time (e.g., resulting in n number of second temperature data entries). By way of example, controller 200 may analyze the first dataset P1 that includes, for example, fifty (50) second temperature data entries (e.g., an n of 50). The controller 200 may generate a second moving average as described above with reference to operation 510 that includes a sum of each second temperature data entry of the first dataset P1 divided by the total number of second temperature data entries n. By way of a particular example, the second moving average may be determined to be 35° C. such that each second temperature data entry (e.g., T21, T22, ..., T250) of the first dataset P1 may be compared against the second moving average.

As described hereafter with reference to operation 615, the controller 200 may operate to count (and subsequently sum) the number of instances in which each second temperature data entry fails to exceed (e.g., is less than) the second moving average (e.g., is <35° C.). As described above, the thermal conductivity of a fluid is greater than that of the air bubble 103. As such, a comparison between each second temperature data entry and the second moving average may identify second temperature data entries that are less than the second moving average of the second temperature sensor 106 that may be indicative of the presence of an air bubble 103 proximate the second temperature sensor 106. Although described herein with reference to a single dataset P1 that includes fifty (50) second temperature data entries and a second moving average of 35° C., the present disclosure contemplates that the operations described herein may be applicable to any number of datasets comprising any number of second temperature data entries and the second moving average may be determined to be any temperature value.

As shown in operation 615, the apparatus (e.g., sensor derive 100 and/or controller 200) includes means, such as processor 202, communications circuitry 208, temperature analysis circuitry 210, or the like, for determining the first air presence parameter as a sum of the number of instances in which each first temperature data entry fails to exceed the first moving average and the number of instances in which each second temperature data entry fails to exceed the second moving average. By way of continued example, the controller 200 may compare, for example, a first temperature value (e.g., first temperature value T11) with the first moving average and a second temperature value (e.g., second temperature value T21) with the second moving average. In an instance in which the first temperature value and/or the second temperature value fail to exceed the first moving average and the second moving average, respectively, the value of the first air presence parameter may be increased (e.g., increased by a count of one (1)). The controller 200 may iteratively perform this comparison for each first temperature value and each second temperature value and sum the number of instances in which each first temperature data entry fails to exceed the first moving average and the number of instances in which each second temperature data entry fails to exceed the second moving average as the first air presence parameter.

Although described herein with reference to a sum of the number of instances in which each first temperature data entry fails to exceed the first moving average and the number of instances in which each second temperature data entry fails to exceed the second moving average, the present disclosure contemplates that the reverse deamination or calculation may occur. Said differently, the controller 200 may instead determine the first air presence parameter as a sum of the number of instances in which each first temperature data entry exceeds the first moving average, and the number of instances in which each second temperature data entry exceeds the second moving average. In such an embodiment, the first air presence parameter may instead determine the presence of fluid within the fluid flow system and identify instances in which there is an absence of fluid as opposed to the presence of air (e.g., detect instantaneous temperature data entries that are not indicative of fluid flow as opposed to indicative of air presence).

As shown in operation 620, the apparatus (e.g., sensor derive 100 and/or controller 200) includes means, such as processor 202, communications circuitry 208, temperature analysis circuitry 210, or the like, for comparing the first air presence parameter with a first parameter threshold. As described above, the first parameter threshold may refer to a minimum portion (e.g., >50%) of the total number of temperature data entries (e.g., n samples×m datasets) against which the first air presence parameter may be compared. By way of continued example, the first parameter threshold may be based upon a single dataset P1 that includes fifty (50) data samples (e.g., fifty (50) first temperature data entries and fifty (50) second temperature data entries). The first parameter threshold may require that, for example, the first air presence parameter be greater than 50% of the total data entries (e.g., greater than 0.5×n×m). In an instance in which the first air presence parameter determined at operation 615 exceeds a first parameter threshold of, for example, twenty-five (25) (e.g., 0.5×50×1), the controller 200 may proceed to perform second air presence parameter determinations as illustrated at operation 625 and described hereafter with reference to FIG. 7. In an instance in which the first air presence parameter determined at operation 615 fails to exceed the first parameter threshold of, for example, twenty-five (25) (e.g., 0.5×50×1), the controller 200 may revert to operation 605 for subsequent datasets (e.g., P2, P3, . . . , Pm).

Figure 7:
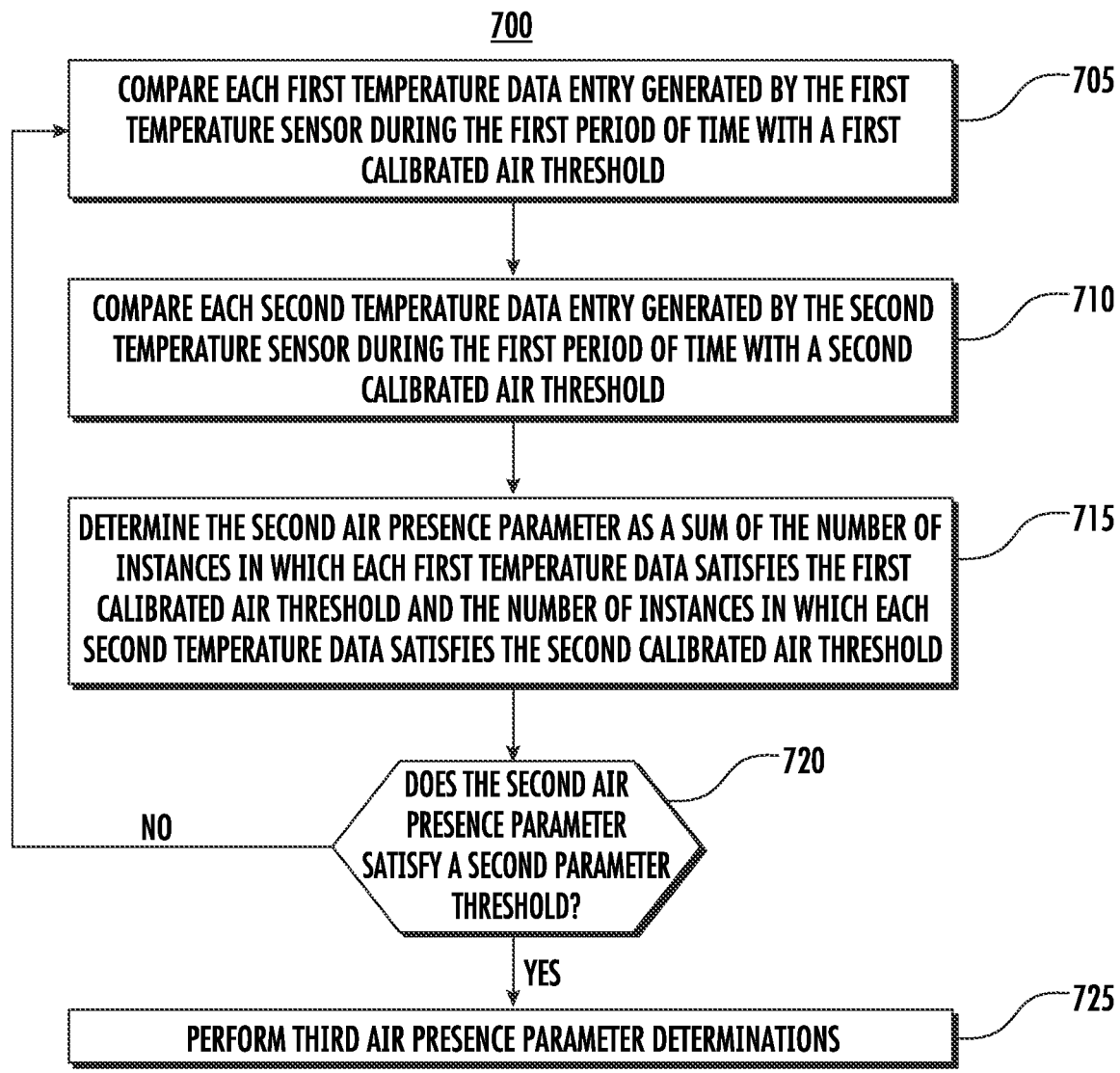
FIG. 7 illustrates an example flowchart for second air presence parameter determinations, in accordance with some example embodiments described herein.

FIG. 7 illustrates a flowchart containing a series of operations second presence parameter determinations. The operations illustrated in FIG. 7 may, for example, be performed by, with the assistance of, and/or under the control of an apparatus (e.g., sensor device 100 and/or controller 200), as described above. In this regard, performance of the operations may invoke one or more of processor 202, memory 204, input/output circuitry 206, communications circuitry 208, and/or temperature analysis circuitry 210.

As shown in operation 705, the apparatus (e.g., sensor derive 100 and/or controller 200) includes means, such as processor 202, communications circuitry 208, temperature analysis circuitry 210, or the like, for comparing each first temperature data entry generated by the first temperature sensor 104 during the first period of time with a first calibrated air threshold. As described above, the first temperature sensor 104 may generate first temperature data entries (e.g., T11, T12, . . . , TiN) as part of a first dataset P1 over a first period of time (e.g., resulting in n number of first temperature data entries). By way of example, controller 200 may analyze a first dataset P1 that includes, for example, fifty (50) first temperature data entries (e.g., an n value of 50). As described above, the sensor device 100 and/or controller 200 may be configured to receive a first calibrated air threshold and/or determine a first calibrated air threshold associated with first temperature sensor 104. By way of example, the fluid flow system 102 may be supplied with air (e.g., an absence of fluid flow) as part of an initial set up or calibration procedure. The first temperature sensor 104 may generate first temperature data during this absence of fluid flow, and these data entries may be used to determine a first calibrated air threshold (e.g., temperature values associated with air as opposed to fluid). By way of a particular example, the first calibrated air threshold may be determined to be substantially 25° C. (e.g., 25° C.±1° C.). The present disclosure contemplates that the first calibrated air threshold may be any calibrated air temperature value and associated margin of error.

As described hereafter with reference to operation 715, the controller 200 may operate to count (and subsequently sum) the number of instances in which each first temperature data entry satisfies the first calibrated air threshold. As described above, the thermal conductivity of a fluid is greater than that of the air bubble 103. As such, a comparison between each first temperature data entry and the first calibrated air threshold may identify first temperature data entries that are similar in temperature to known air temperature values and may be indicative of the presence of an air bubble 103 proximate the first temperature sensor 104. Although described herein with reference to a single dataset P1 that includes fifty (50) first temperature data entries and a first calibrated air threshold of 25° C., the present disclosure contemplates that the operations described herein may be applicable to any number of datasets comprising any number of first temperature data entries and the first calibrated air threshold may be determined to be any temperature value.

As shown in operation 710, the apparatus (e.g., sensor derive 100 and/or controller 200) includes means, such as processor 202, communications circuitry 208, temperature analysis circuitry 210, or the like, for comparing each second temperature data entry generated by the second temperature sensor 106 during the first period of time with a second calibrated air threshold. As described above, the second temperature sensor 106 may generate second temperature data entries (e.g., T21, T22, . . . , T2N) as part of a first dataset P1 over a first period of time (e.g., resulting in n number of second temperature data entries). By way of example, controller 200 may analyze a first dataset P1 that includes, for example, fifty (50) second temperature data entries (e.g., an n value of 50). As described above, the sensor device 100 and/or controller 200 may be configured to receive a second calibrated air threshold and/or determine a second calibrated air threshold associated with second temperature sensor 106. By way of example, the fluid flow system 102 may be supplied with air (e.g., an absence of fluid flow) as part of an initial set up or calibration procedure. The second temperature sensor 106 may generate second temperature data during this absence of fluid flow and these data entries may be used to determine a second calibrated air threshold (e.g., temperature values associated with air as opposed to fluid). By way of a particular example, the second calibrated air threshold may be determined to be substantially 30° C. (e.g., 30° C.±1° C.). The present disclosure contemplates that the second calibrated air threshold may be any calibrated air temperature value and associated margin of error.

As described hereafter with reference to operation 715, the controller 200 may operate to count (and subsequently sum) the number of instances in which each second temperature data entry satisfies the second calibrated air threshold. As described above, the thermal conductivity of a fluid is greater than that of the air bubble 103. As such, a comparison between each second temperature data entry and the second calibrated air threshold may identify second temperature data entries that are similar in temperature to known air temperature values and may be indicative of the presence of an air bubble 103 proximate the second temperature sensor 106. Although described herein with reference to a single dataset P1 that includes fifty (50) second temperature data entries and a second calibrated air threshold of 30° C., the present disclosure contemplates that the operations described herein may be applicable to any number of datasets comprising any number of second temperature data entries and the second calibrated air threshold may be determined to be any temperature value.

As shown in operation 715, the apparatus (e.g., sensor derive 100 and/or controller 200) includes means, such as processor 202, communications circuitry 208, temperature analysis circuitry 210, or the like, for determining the second air presence parameter as a sum of the number of instances in which each first temperature data satisfies the first calibrated air threshold and the number of instances in which each second temperature data satisfies the second calibrated air threshold. By way of continued example, the controller 200 may compare, for example, a first temperature value (e.g., first temperature value T11) with the first calibrated air threshold and a second temperature value (e.g., second temperature value T21) with the second calibrated air threshold. In an instance in which the first temperature value and the second temperature value are substantially the same as the first calibrated air threshold and the second calibrated air threshold, respectively, the value of the second air presence parameter may be increased (e.g., increased by a count of one (1)). The controller may iteratively perform this comparison for each first temperature value and each second temperature value and sum the number of instances in which each first temperature data satisfies (e.g., is substantially the same as) the first calibrated air threshold and the number of instances in which each second temperature data satisfies (e.g., is substantially the same as) the second calibrated air threshold as the second air presence parameter.

As shown in operation 720, the apparatus (e.g., sensor derive 100 and/or controller 200) includes means, such as processor 202, communications circuitry 208, temperature analysis circuitry 210, or the like, for comparing the second air presence parameter with a second parameter threshold. As described above, the second parameter threshold may refer to a minimum portion (e.g., >50%) of the total number of temperature data entries (e.g., n samples×m datasets) against which the second air presence parameter may be compared. By way of continued example, the second parameter threshold may be based upon a single dataset P1 that includes fifty (50) data samples (e.g., fifty (50) first temperature data entries and fifty (50) second temperature data entries). The second parameter threshold may require that, for example, that the second air presence parameter be greater than 50% of the total data entries (e.g., greater than 0.5×n×m). In an instance in which the second air presence parameter determined at operation 715 exceeds a second parameter threshold of, for example, twenty-five (25) (e.g., 0.5×50×1), the controller may proceed to perform third air presence parameter determinations as illustrated at operation 725 and described hereafter with reference to FIG. 8. In an instance in which the second air presence parameter determined at operation 715 fails to exceed the second parameter threshold of, for example, twenty-five (25) (e.g., 0.5×50×1), the controller may revert to operation 705 for subsequent datasets (e.g., P2, P3, . . . , Pm).

Figure 8:
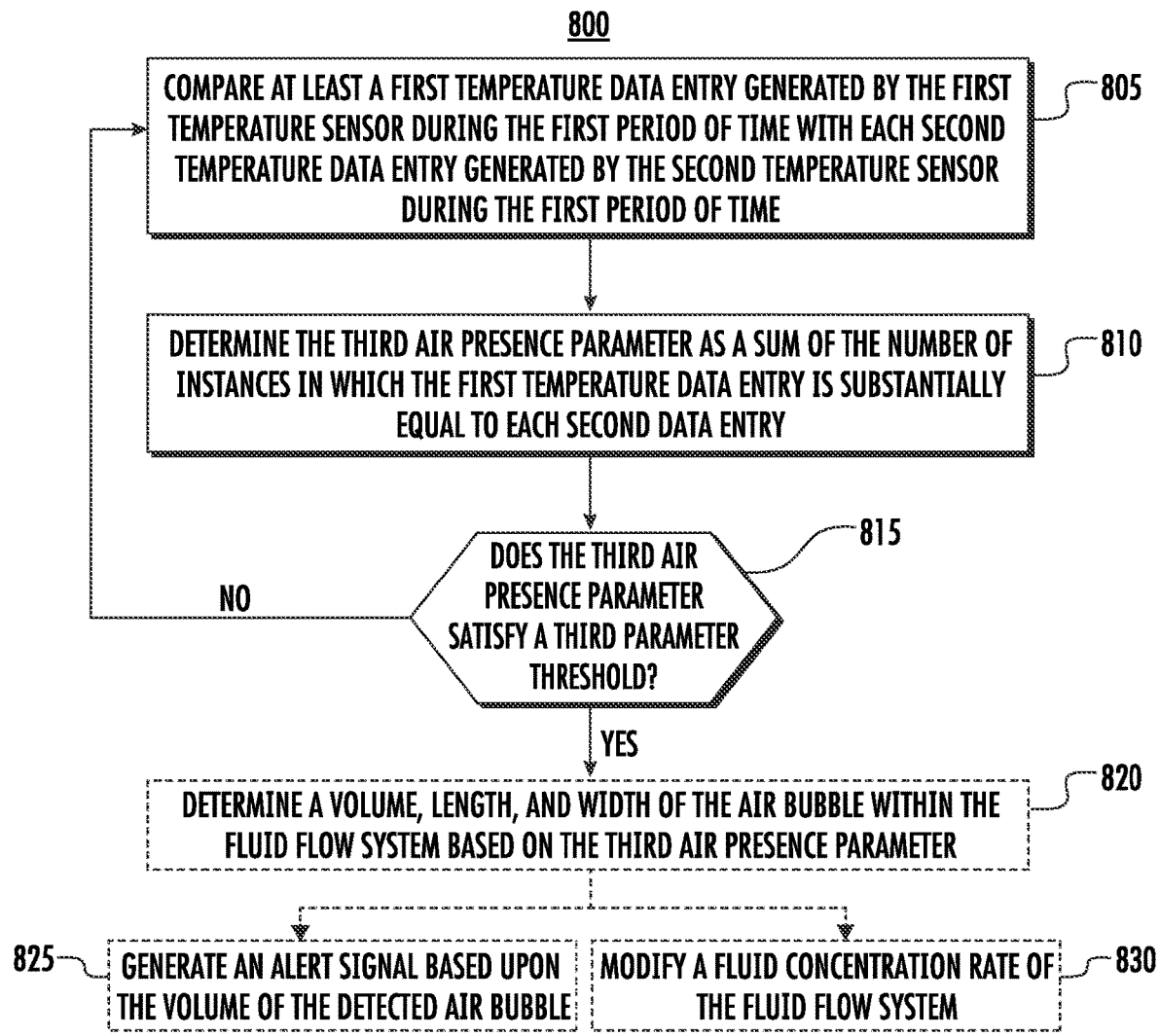
FIG. 8 illustrates an example flowchart for third air presence parameter determinations, in accordance with some example embodiments described herein.

FIG. 8 illustrates a flowchart containing a series of operations for third air presence parameter determinations. The operations illustrated in FIG. 8 may, for example, be performed by, with the assistance of, and/or under the control of an apparatus (e.g., controller 200), as described above. In this regard, performance of the operations may invoke one or more of processor 202, memory 204, input/output circuitry 206, communications circuitry 208, and/or temperature analysis circuitry 210.

As shown in operation 805, the apparatus (e.g., sensor derive 100 and/or controller 200) includes means, such as processor 202, communications circuitry 208, temperature analysis circuitry 210, or the like, for comparing at least a first temperature data entry generated by the first temperature sensor 104 during the first period of time with each second temperature data entry generated by the second temperature sensor 106 during the first period of time. As described above, the first temperature sensor 104 may generate first temperature data entries (e.g., T11, T12, . . . , TiN) as part of a first dataset P1 over a first period of time (e.g., resulting in n number of first temperature data entries). By way of example, controller 200 may analyze a first dataset P1 that includes, for example, fifty (50) first temperature data entries (e.g., an n value of 50). Similarly, the second temperature sensor 106 may generate second temperature data entries (e.g., T21, T22, . . . , T2N) as part of a first dataset P1 over a first period of time (e.g., resulting in n number of second temperature data entries). By way of example, controller 200 may analyze a first dataset P1 that includes, for example, fifty (50) second temperature data entries (e.g., an n value of 50). In order to identify a shift in momentary temperate change indicative of the leading and/or trailing edges of the air bubble 103 (e.g., the front edge of the air bubble 103), the first temperature data entries may each be compared with the second temperature data entries in order to identify instances in which the first temperature data entry is substantially equal to at least one second data entry. Said differently, first temperature data entries that are substantially equal to second temperature data entries may be indicative of the same relative position of the air bubble 103.

As shown in operation 810, the apparatus (e.g., sensor derive 100 and/or controller 200) includes means, such as processor 202, communications circuitry 208, temperature analysis circuitry 210, or the like, for determining the third air presence parameter as a sum of the number of instances in which the first temperature data entry is substantially equal to at least one of the second data entry. By way of continued example, the controller 200 may compare, for example, a first temperature value (e.g., first temperature value T11) with each second temperature value (e.g., second temperature value T21, T22, . . . , T250). In an instance in which the first temperature value and the second temperature value are substantially the same, the value of the third air presence parameter may be increased (e.g., increased by a count of one (1)). The controller may iteratively perform this comparison for each first temperature value and each second temperature value and sum the number of instances in which each first temperature data satisfies (e.g., is substantially the same as) the second temperature data as the third air presence parameter.

As shown in operation 815, the apparatus (e.g., sensor derive 100 and/or controller 200) includes means, such as processor 202, communications circuitry 208, temperature analysis circuitry 210, or the like, for comparing the third air presence parameter with a third parameter threshold. As described above, the third parameter threshold may refer to a minimum portion (e.g., >50%) of the total number of temperature data entries (e.g., n samples×m datasets) against which the third air presence parameter may be compared. By way of continued example, the third parameter threshold may be based upon a single dataset P1 that includes fifty (50) data samples (e.g., fifty (50) first temperature data entries and fifty (50) second temperature data entries). The third parameter threshold may require that, for example, that the third air presence parameter be greater than 50% of the total data entries (e.g., greater than 0.5×n×m). In an instance in which the third air presence parameter determined at operation 810 exceeds a third parameter threshold of, for example, twenty-five (25) (e.g., 0.5×50×1), the controller may detect the presence of an air bubble in the fluid flow system 102. Said differently, in an instance in which the first air presence parameter satisfies the first parameter threshold, in which the second air presence parameter satisfies the second parameter threshold, and in which the third air presence parameter satisfies the third parameter threshold, the controller may detect the presence of an air bubble in the fluid flow system 102. The present disclosure contemplates that each of the first parameter threshold, the second parameter threshold, and the third parameter threshold may be modified based upon the intended application of the sensor device 100 (e.g., >60%, >70%, >80%, etc. of the total temperature data entries.

In some embodiments, as shown in operation 820, the apparatus (e.g., sensor derive 100 and/or controller 200) includes means, such as processor 202, communications circuitry 208, temperature analysis circuitry 210, or the like, for determining a volume, length, and width of the air bubble 103 within the fluid flow system 102 based on the third air presence parameter. By way of example, the controller 200 may quantify the air bubble size and volume by first averaging the values associated with the first air presence parameter, the second air presence parameter, the third air presence parameter. The controller 200 may further multiple the averaged air presence parameter value with the flow velocity of the fluid flow system 102 and divide by the number of data samples multiplied by the number of datasets and the sampling time (e.g., flow velocity/(n×m×sampling time)). Such a calculation may provide the average length of the air bubble 103 and the volume of the air bubble 103. By way of an additional example, the controller 200 may be supplied with data indicative of the diameter of a tube (e.g., conduit of the fluid flow system 102), and the controller may determine, from the third air presence parameter, the time elapsed time lapsed during which the bubble is located in the tube. This time may be multiplied by sampling rate, for example, to provide bubble length.

In some further embodiments, as shown in operation 825, the apparatus (e.g., sensor derive 100 and/or controller 200) includes means, such as processor 202, communications circuitry 208, temperature analysis circuitry 210, or the like, for generating an alert signal based upon the volume of the detected air bubble 103. By way of example, in some embodiments, the detection of the air bubble 103 described herein may further include a volume determination. Such a volume determination (e.g., operation 820) may, in some embodiments, indicate that the volume of the air bubble 103 is sufficiently large (e.g., exceeds a threshold value) such that damage to the fluid flow system 102, to a human patient connected to the fluid flow system, or the like may occur. As such, the controller 200 may be configured to generate an alert signal indicating the presence of the air bubble 103 to, for example, a human operator associated with the fluid flow system 102.

In some further embodiments, as shown in operation 830, the apparatus (e.g., sensor derive 100 and/or controller 200) includes means, such as processor 202, communications circuitry 208, temperature analysis circuitry 210, or the like, for modify a fluid concentration rate of the fluid flow system 102. By way of example, in some embodiments, the detection of the air bubble 103 described herein may further include a volume determination. Such a volume determination (e.g., operation 820) may, in some embodiments, indicate that the volume of the air bubble 103 is sufficient (e.g., exceeds a threshold value) to alter the concentration of the fluid supplied by the fluid flow system 102 (e.g., reduce the concentration of a pharmaceutical solution). As such, the controller 200 may be configured to modify a fluid concentration of the fluid flow system by, for example, causing additional pharmaceutical compounds to be supplied to the fluid flow system 102 to address any concentration deficiency as described above.

FIGS. 5-8 thus illustrate flowcharts describing the operation of apparatuses, methods, and computer program products according to example embodiments contemplated herein. It will be understood that each flowchart block, and combinations of flowchart blocks, may be implemented by various means, such as hardware, firmware, processor, circuitry, and/or other devices associated with execution of software including one or more computer program instructions. For example, one or more of the operations described above may be implemented by an apparatus executing computer program instructions. In this regard, the computer program instructions may be stored by a memory 204 of the controller 200 and executed by a processor 202 of the controller 200. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture, the execution of which implements the functions specified in the flowchart blocks. The computer program instructions may also be loaded onto a computer or other programmable apparatus to cause a series of operations to be performed on the computer or other programmable apparatus to produce a computer-implemented process such that the instructions executed on the computer or other programmable apparatus provide operations for implementing the functions specified in the flowchart blocks.

The flowchart blocks support combinations of means for performing the specified functions and combinations of operations for performing the specified functions. It will be understood that one or more blocks of the flowcharts, and combinations of blocks in the flowcharts, can be implemented by special purpose hardware-based computer systems which perform the specified functions, or combinations of special purpose hardware with computer instructions.

What is claimed is:

1. A sensor device for use with fluid flow systems, the sensor device comprising:
a heating element;
a first temperature sensor configured to generate first temperature data;
a second temperature sensor configured to generate second temperature data, wherein the heating element, the first temperature sensor, and the second temperature sensor are thermally coupled with a fluid flow system; and
a controller operably coupled with the heating element, the first temperature sensor, and the second temperature sensor, wherein the controller is configured to:
determine a first moving average for a first period of time based upon the first temperature data generated by the first temperature sensor during the first period of time;
determine a second moving average for the first period of time based upon the second temperature data generated by the second temperature sensor during the first period of time; and
detect presence of an air bubble within the fluid flow system based upon the first moving average, the second moving average, and one or more calibrated air thresholds.

2. The sensor device according to claim 1, wherein the second temperature sensor is positioned downstream of the heating element, and the heating element is positioned downstream of a first temperature system relative to a fluid flow direction of the fluid flow system.

3. The sensor device according to claim 2, wherein the first temperature sensor comprises a first pair of offset thermopiles, and the second temperature sensor comprises a second pair of offset thermopiles.

4. The sensor device according to claim 1, wherein the controller is further configured to:
compare each first temperature data entry generated by the first temperature sensor during the first period of time with the first moving average;
compare each second temperature data entry generated by the second temperature sensor during the first period of time with the second moving average;
determine a first air presence parameter as a sum of a number of instances in which each first temperature data entry fails to exceed the first moving average and a number of instances in which each second temperature data entry fails to exceed the second moving average; and
compare the first air presence parameter with a first parameter threshold.

5. The sensor device according to claim 4, wherein the controller is further configured to:
compare each first temperature data entry generated by the first temperature sensor during the first period of time with a first calibrated air threshold;
compare each second temperature data entry generated by the second temperature sensor during the first period of time with a second calibrated air threshold;
determine a second air presence parameter as a sum of a number of instances in which each first temperature data satisfies the first calibrated air threshold and a number of instances in which each second temperature data satisfies the second calibrated air threshold; and
compare the second air presence parameter with a second parameter threshold.

6. The sensor device according to claim 5, wherein the controller is further configured to:
compare at least a first temperature data entry generated by the first temperature sensor during the first period of time with each second temperature data entry generated by the second temperature sensor during the first period of time;
determine a third air presence parameter as a sum of a number of instances in which the first temperature data entry is substantially equal to each second data entry;
compare the third air presence parameter with a third parameter threshold; and
detect the presence of the air bubble based upon the first air presence parameter, the second air presence parameter, and the third air presence parameter.

7. The sensor device according to claim 6, wherein the controller is further configured to determine a volume, length, and width of the air bubble within the fluid flow system based on the third air presence parameter.

8. The sensor device according to claim 7, wherein the controller is further configured to modify a fluid concentration rate of the fluid flow system or generate an alert signal based upon the volume of the detected air bubble.

9. A method for air bubble detection comprising:
determining a first moving average for a first period of time based upon first temperature data generated by a first temperature sensor during the first period of time;
determining a second moving average for the first period of time based upon second temperature data generated by a second temperature sensor during the first period of time; and
detecting presence of an air bubble within a fluid flow system based upon the first moving average, the second moving average, and one or more calibrated air thresholds.

10. The method according to claim 9, wherein the second temperature sensor is positioned downstream of a heating element and the heating element is positioned downstream of a first temperature system as related to the fluid flow system.

11. The method according to claim 9, further comprising:
comparing each first temperature data entry generated by the first temperature sensor during the first period of time with the first moving average;
comparing each second temperature data entry generated by the second temperature sensor during the first period of time with the second moving average;
determining a first air presence parameter as a sum of a number of instances in which each first temperature data entry fails to exceed the first moving average and a number of instances in which each second temperature data entry fails to exceed the second moving average; and
comparing the first air presence parameter with a first parameter threshold.

12. The method according to claim 11, further comprising:
comparing each first temperature data entry generated by the first temperature sensor during the first period of time with a first calibrated air threshold;
comparing each second temperature data entry generated by the second temperature sensor during the first period of time with a second calibrated air threshold;
determining a second air presence parameter as a sum of a number of instances in which each first temperature data satisfies the first calibrated air threshold and a number of instances in which each second temperature data satisfies the second calibrated air threshold; and comparing the second air presence parameter with a second parameter threshold.

13. The method according to claim 12, further comprising:

comparing at least a first temperature data entry generated by the first temperature sensor during the first period of time with each second temperature data entry generated by the second temperature sensor during the first period of time;

determining a third air presence parameter as a sum of a number of instances in which the first temperature data entry is substantially equal to each second data entry;

comparing the third air presence parameter with a third parameter threshold; and detecting the presence of the air bubble based upon the first air presence parameter, the second air presence parameter, and the third air presence parameter.

14. The method according to claim 13, further comprising determining a volume, length, and width of the air bubble within the fluid flow system based on the third air presence parameter.

15. The method according to claim 14, further comprising modifying a fluid concentration rate of the fluid flow system or generating an alert signal based upon the volume of the detected air bubble.

16. A non-transitory computer-readable storage medium for using an apparatus to provide air bubble detection, the non-transitory computer-readable storage medium storing instructions that, when executed, cause the apparatus to:

determine a first moving average for a first period of time based upon first temperature data generated by a first temperature sensor during the first period of time;

determine a second moving average for the first period of time based upon second temperature data generated by a second temperature sensor during the first period of time; and detect presence of an air bubble within a fluid flow system based upon the first moving average, the second moving average, and one or more calibrated air thresholds.

17. The non-transitory computer-readable storage medium according to claim 16, wherein the non-transitory computer-readable storage medium stores instructions that, when executed, cause the apparatus to:

compare each first temperature data entry generated by the first temperature sensor during the first period of time with the first moving average;

compare each second temperature data entry generated by the second temperature sensor during the first period of time with the second moving average;

determine a first air presence parameter as a sum of a number of instances in which each first temperature data entry fails to exceed the first moving average and a number of instances in which each second temperature data entry fails to exceed the second moving average; and compare the first air presence parameter with a first parameter threshold.

18. The non-transitory computer-readable storage medium according to claim 17, wherein the non-transitory computer-readable storage medium stores instructions that, when executed, cause the apparatus to:

compare each first temperature data entry generated by the first temperature sensor during the first period of time with a first calibrated air threshold;

compare each second temperature data entry generated by the second temperature sensor during the first period of time with a second calibrated air threshold;

determine a second air presence parameter as a sum of a number of instances in which each first temperature data satisfies the first calibrated air threshold and a number of instances in which each second temperature data satisfies the second calibrated air threshold; and compare the second air presence parameter with a second parameter threshold.

19. The non-transitory computer-readable storage medium according to claim 18, wherein the non-transitory computer-readable storage medium stores instructions that, when executed, cause the apparatus to:

compare at least a first temperature data entry generated by the first temperature sensor during the first period of time with each second temperature data entry generated by the second temperature sensor during the first period of time;

determine a third air presence parameter as a sum of a number of instances in which the first temperature data entry is substantially equal to each second data entry;

compare the third air presence parameter with a third parameter threshold; and detect the presence of the air bubble based upon the first air presence parameter, the second air presence parameter, and the third air presence parameter.

20. The non-transitory computer-readable storage medium according to claim 19, wherein the non-transitory computer-readable storage medium stores instructions that, when executed, cause the apparatus to determine a volume, length, and width of the air bubble within the fluid flow system based on the third air presence parameter.

* * * * *